(12) United States Patent
Conceicao et al.

(10) Patent No.: US 7,202,397 B2
(45) Date of Patent: Apr. 10, 2007

(54) CHALCONE SYNTHASE

(75) Inventors: Alexandre da Silva Conceicao, Wilmington, DE (US); Leslie T. Harvell, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 464 days.

(21) Appl. No.: 10/641,495

(22) Filed: Aug. 15, 2003

(65) Prior Publication Data

US 2004/0181823 A1    Sep. 16, 2004

Related U.S. Application Data

(60) Provisional application No. 60/404,171, filed on Aug. 16, 2002.

(51) Int. Cl.
| | |
|---|---|
| C12N 15/29 | (2006.01) |
| C12N 15/52 | (2006.01) |
| C12N 15/82 | (2006.01) |
| A01H 5/00 | (2006.01) |
| A01H 5/10 | (2006.01) |

(52) U.S. Cl. .................. 800/298; 536/23.1; 536/23.2; 536/23.6; 435/230.1; 435/419

(58) Field of Classification Search ................ 800/278, 800/298; 536/23.1, 23.2, 23.6; 435/419, 435/320.1
See application file for complete search history.

(56) References Cited

U.S. PATENT DOCUMENTS 6,037,523 A    3/2000   Albertsen et al.

OTHER PUBLICATIONS

Doerks et al., (TIG, 1998, vol. 14, No. 6; pp. 248-250.*
Smith T. et al. (Nature Biotechnology, Nov. 1997, vol. 15; pp. 1222-1223.*
Brenner S. et al. (TIG, Apr. 1999, vol. 15, No. 4; pp. 132-133).*
Bork P. et al. (TIG, Oct. 1996, vol. 12, No. 10; pp. 425-427).*
Venter C. et al., (Science, 2001; vol. 291, pp. 1304-1351).*
Dixon R. et al. Trends in Plant Science, Oct. 1999; vol. 4, No. 10, pp. 1360-1385.*
Elomaa P. et al., Molecular Breeding 1996, 2: pp. 41-50.*
Anne-Catherine Claudot et al., Preparation and Assay of Chalcone Synthase from Walnut Tree Tissue, Phytochemistry, vol. 31(10):3377-3380, 1992.
Karin W. M. Zuurbier et al., Assay of Chalcone Synthase Activity by High-Performance Liquid Chromatography, Phytochemistry, vol. 34(5):1225-1229, 1993.
Anne-Catherine Claudot et al., Cloning and characterization of two memebers of the chalcone synthase gene family from walnut, Plant Physiol. Biochem., 37(10):721-730, 1999.
National Center for Biotechnology Information General Identifier No. 1296816, Accession No. CAA64452, Nov. 19, 1999, A. C. Claudot et al., Cloning and characterization of two memebers of the chalcone synthase gene family from walnut.
Ingrid M. Van Der Meer et al., Antisense Inhibition of Flavonoid Biosynthesis in Petunia Anthers Results in Male Sterility, The Plant Cell, vol. 4:253-262, 1992.
Richard A. Dixon et al., Stress-Induced Phenylpropanoid Metabolism, The Plant Cell, vol. 7:1085-1097, 1995.
Yukako Hihara et al., Isolation and characterization of two cDNA clones for mRNAs that are abundantly expressed in immature anthers of rice (Oryza sativa L.), Plant Mol. Biol., vol. 30:1181-1193, 1996.
Ruth Wingender et al., Differential regulation of soybean chalcone synthase genes in plant defence, symbiosis and upon environmental stimuli, Mol. Gen. Genet., vol. 218:315-322, 1989.
National Center for Biotechnology Information General Identifier No. 50508513, Accession No. BAD30758, Jul. 22, 2004.
Miriam G.G. Contessotto et al., Genetics Mol. Biol., vol. 24(1-4):257-261, 2001, A New Member of the Chalcone Synthase (CHS) Family in Sugarcane.
Thomas Lanz et al., J. Biol. Chem., vol. 226(15):9971-9976, 1991, The Role of Cysteines in Polyketide Synthases.
Joseph M. Jez et al., J. Biol. Chem., vol. 275(50):39640-39646, 2000, Mechanism of Chalcone Synthase.

* cited by examiner

*Primary Examiner*—Russell P. Kallis

(57) ABSTRACT

An isolated nucleic acid fragment encoding a chalcone synthase is disclosed. Construction of a recombinant DNA construct encoding all or a portion of the chalcone synthase, in sense or antisense orientation, wherein expression of the recombinant DNA construct results in production of altered levels of the chalcone synthase in a transformed host cell are also discussed.

11 Claims, 3 Drawing Sheets

Figure 2A

Figure 1:
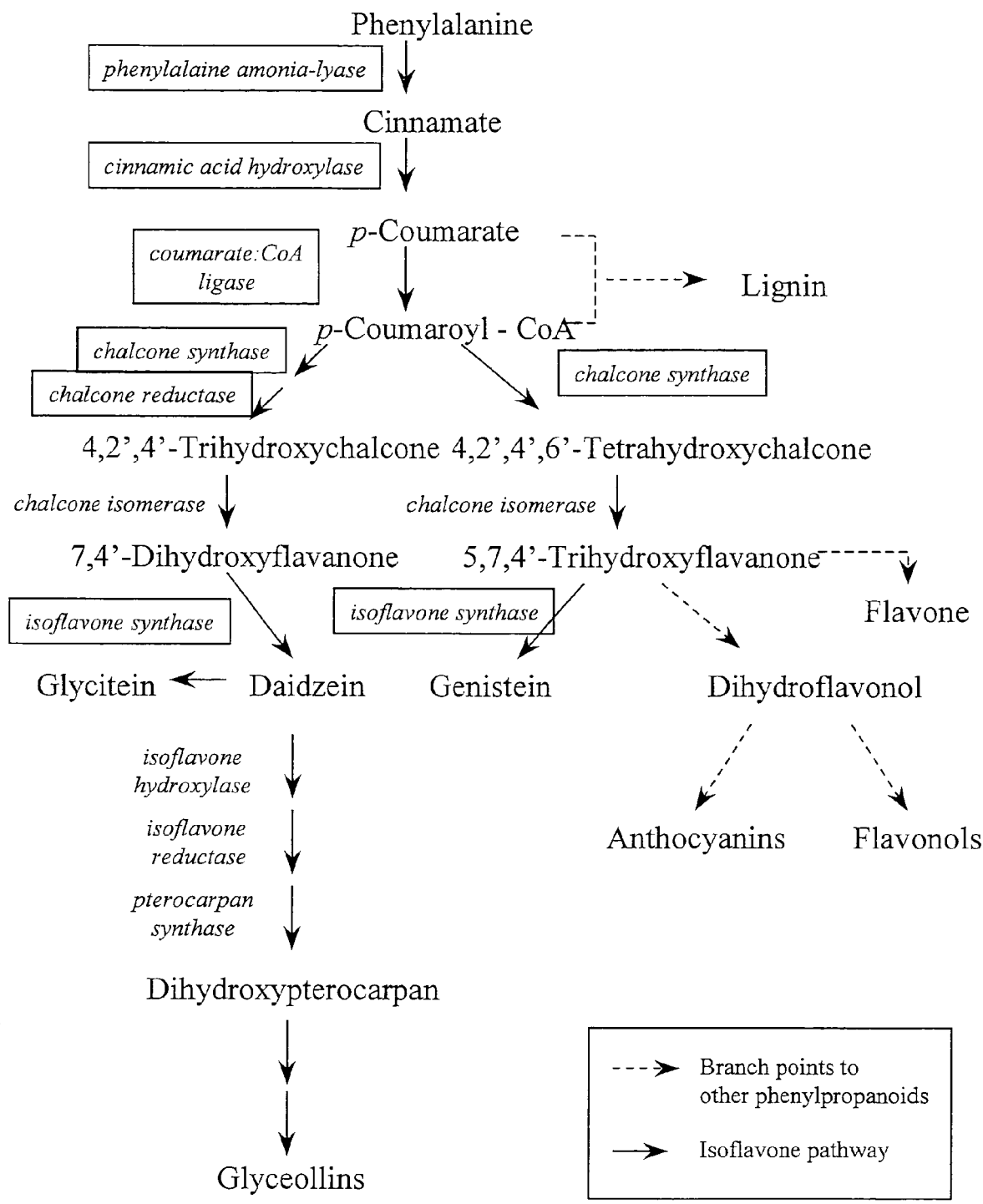

```
                                                                          60
SEQ ID NO:5   -----MVTVEDVRRAQRAEGPATVMAIGTATPPNCVDQSAYPDYYFRITNSEHKTELKEK
SEQ ID NO:2   MGSNTLTSMHEIRRLQRAEGPAAILAVGTANPPNCVSQEEYPDYYFRVTKSEHLTDLKQK
SEQ ID NO:4   ARG-------RAQRADGPAAVLAIGTANPAHCVPQDEFPDYFRATNSDHLTALKGK 61                                                              120
SEQ ID NO:5   FKRMCEKSMIKKRYMHLTEEILKENPNVCAYMASSLDARQDMVVVEVPKLGKEAATKAIK
SEQ ID NO:2   LKSFCQMTSTEKRYFHHTEELLDAHPEFLRRDTPSLDARLDIAAAAAPELAASAAAKAIA
SEQ ID NO:4   FKRVFQKLGVEKRYLHHTEELLRAHPEFLDDEAASLDARLDIVATAVPELAAEEASKKAIS 121                                                              180
SEQ ID NO:5   EWGQPKSKITHLVFCTTSGVDMPGADYQLTKLLGLRPSVKRLMMYQQGCFAGGTVLRLAK
SEQ ID NO:2   EWGRPATDITHLVVSTNSGAHAPGVDLRLASLLGLRASVCRTMLNLNGCSAGAASLRLAK
SEQ ID NO:4   EWGRPAADITHLVVTTNSGAHIPGVDFRLIPLLGLRPSVRRTMLYLNGCFAGSAALRLAK 181                                                              240
SEQ ID NO:5   DLAENNKGARVLVVCSEITAVTFRGPSDTHLDSLVGQALFGDGAAALIVGADPVPGVEKP
SEQ ID NO:2   DLAENNRGARVLVVACVELTVVAFRGPEEAYPHRLISQAIFGDGAGAVIVGADAVRSVERP
SEQ ID NO:4   DLAENNRGARVLVVCAELTLMLFNGPKEGSFERLIHQGLFGDGAGAVVVGADPLSPVEHA 241                                                              300
SEQ ID NO:5   LFELVSAAQTILPDSDGAIDGHLREVGLTFHLL-KDVPGLISKNIEKSLVEAFQPLGI--
SEQ ID NO:2   LFEMVSASQTTIPATDGVLTMQLTEAGLDGDIFTRELTPLAAQHIEQCLTDAFQPLGIMS
SEQ ID NO:4   LFEMVSAAQTVIPDSGDAITMHITKGGFGGNISTRDVPVFIGDNVERCLHDSLEPLGI--
```

Figure 2B

```
         301                                                        360
SEQ ID NO:5  --TDWNSLFWIAHPGGPAILDQVESKLELKPEKLRATRHVLSEYGNMSSACVLFILDEMR
SEQ ID NO:2  GGAEWNDLFFVVHPGLRGIMDHIDGALRLDPGKLVASRTVLREYGNMLGATLIFVLDEQR
SEQ ID NO:4  -GAKWNDLFWAVHPGSSAILDRIDTVLQLEPEKLAASRRVLSDYGNMFGVTIIFVLDELR 361                                                        405
SEQ ID NO:5  KKSAEDRLKTTGEGLEWGVLFGFGPGLTVETVVLHSVS------A
SEQ ID NO:2  RRMEED--GETG---EWGVMMGFGPGFTVETMVLHAVAIDLHNEN
SEQ ID NO:4  RRLREQ--EGAGGAPEWGVVMTFGPGLTVETMVLHATG-HMHASP
```

US 7,202,397 B2

CHALCONE SYNTHASE

This application claims the benefit of U.S. Provisional Application Ser. No. 60/404,171, filed Aug. 16, 2002, the entire content of which is herein incorporated by reference.

FIELD OF INVENTION

The field of invention relates to plant molecular biology, and in particular, to nucleic acid fragments encoding chalcone synthase in plants and seeds.

BACKGROUND OF INVENTION

All phenylpropanoids are derived from cinnamic acid, which is formed from phenylalanine by the action of phenylalanine ammonia-lyase, the branch point between primary and secondary metabolism. Isoflavones represent a class of secondary metabolites produced in plants by the phenylpropanoid biosynthesis pathway. The biosynthetic pathway for free isoflavones and their relationship with several other classes of phenylpropanoids is presented in FIG. 1.

Chalcone synthase (E.C. 2.3.1.74) is the first enzyme in the flavonoid-specific branch of the phenylpropanoid biosynthetic pathway (Dixon et al., *Plant Cell* 7:1085–1097 (1995)). As such it is a key enzyme in secondary metabolism. Chalcone synthase catalyzes the condensation of p-coumaroyl-coenzyme A and three molecules of malonyl-coenzyme A. In most plant families, the initial product of chalcone synthase is a tetrahydroxychalcone, which is further converted into other flavonoid classes. In legumes, which possess chalcone reductase as well as chalcone synthase, a trihydroxychalcone may be formed. Compounds resulting from chalcone synthase are important in several physiological processes, including wound response, defense against microbial infection via production of isoflavonoid phytoalexins, UV-B protectants and nodulation in legumes.

Chalcone synthase (Registry Number 180391-56-4) has been associated with expression in anthers of rice (*Oryza sativa*) at the uninucleate microspore stage (Hihara et al., *Plant Mol. Biol.* 30(6):1181–1193 (1996)). Male sterility may be induced by the inhibition of flavenoid biosythesis using an expression vector that produces antisense RNA for the 3' untranslated region of chalcone synthase A gene (see U.S. Pat. No. 6,037,523, column 12, lines 21–25, referencing Van der Meer, et al., *The Plant Cell, Vol.* 4; pp. 253; (1992)). In soybean (*Glycine max*), six isoforms of chalcone synthase originating from different messenger RNAs have been reported (Wingender et al., *Mol. Gen. Genet.* 218: 315–322 (1989)). To date, no chalcone synthase has been isolated from wheat (*Triticum aestivum*).

SUMMARY OF INVENTION

The present invention includes isolated polynucleotides comprising a nucleotide sequence encoding a polypeptide having chalcone synthase activity wherein the amino acid sequence of the polypeptide and the amino acid sequence of SEQ ID NO:2 or 4 have preferably at least 80% sequence identity, preferably based on the Clustal method of alignment. It is more preferred that the identity be at least 85%, even more preferred if the identity is at least 90%, and it is most preferred that the identity be at least 95%. The present invention also includes isolated polynucleotides comprising the full-length complement of the nucleotide sequence. More preferably, the present invention includes isolated polynucleotides encoding the polypeptide sequence of SEQ ID NO:2 or 4 or nucleotide sequences comprising the nucleotide sequence of SEQ ID NO:1 or 3.

The present invention also includes:

in a preferred first embodiment, an isolated polynucleotide comprising: (a) a nucleotide sequence encoding a polypeptide having chalcone synthase activity, wherein the amino acid sequence of the polypeptide and the amino acid sequence of SEQ ID NO:2 or 4 have at least 80%, 85%, 90%, or 95% identity, preferably based on the Clustal method of alignment, or (b) the complement of the nucleotide sequence of (a); the polypeptide preferably comprises the amino acid sequence of SEQ ID NO:2 or 4; the nucleotide sequence preferably comprises the nucleotide sequence of SEQ ID NO:1 or 3; the polypeptide preferably has chalcone synthase activity;

in a preferred second embodiment, a vector comprising any of the isolated polynucleotides of the present invention;

in a preferred third embodiment, a recombinant DNA construct comprising any of the isolated polynucleotides of the present invention operably linked to at least one regulatory sequence, and a cell, a plant, and a seed comprising the recombinant DNA construct;

in a preferred fourth embodiment, a method for transforming a cell comprising transforming a cell with any of the isolated polynucleotides or recombinant DNA constructs of the present invention, and the cell transformed by this method; advantageously, the cell is eukaryotic, e.g., a yeast or plant cell, or prokaryotic, e.g., a bacterium;

in a preferred fifth embodiment, a method for producing a transgenic plant comprising transforming a plant cell with any of the isolated polynucleotides or recombinant DNA constructs of the present invention and regenerating a plant from the transformed plant cell, a transgenic plant produced by this method, and seed obtained from this transgenic plant;

in a preferred sixth embodiment, a first nucleotide sequence which contains at least 30 nucleotides, and wherein the first nucleotide sequence is comprised by another polynucleotide, wherein the other polynucleotide includes: (a) a second nucleotide sequence, wherein the second nucleotide sequence encodes a polypeptide having chalcone synthase activity, wherein the amino acid sequence of the polypeptide and the amino acid sequence of SEQ ID NO:2 or 4 have at least 80% sequence identity, preferably based on the Clustal method of alignment, or (b) the complement of the second nucleotide sequence of (a);

in a preferred seventh embodiment, an isolated polypeptide comprising an amino acid sequence having chalcone synthase activity, wherein the amino acid sequence and the amino acid sequence of SEQ ID NO:2 or 4 have at least 80%, 85%, 90%, or 95% sequence identity, preferably based on the Clustal method of alignment; the amino acid sequence preferably comprises the amino acid sequence of SEQ ID NO:2 or 4; the polypeptide preferably has chalcone synthase activity;

in a preferred eighth embodiment, a method for isolating a polypeptide comprising isolating the polypeptide from a cell or culture medium of the cell, wherein the cell comprises a recombinant DNA construct comprising a polynucleotide of the present invention operably linked to at least one regulatory sequence.

BRIEF DESCRIPTION OF THE DRAWINGS AND SEQUENCE LISTINGS

The invention can be more fully understood from the following detailed description and the accompanying drawings and Sequence Listing which form a part of this application.

FIG. 1 depicts the phenylpropanoid metabolic pathway illustrating the biosynthesis of isoflavones.

FIGS. 2A and 2B show a comparison of (i) the amino acid sequences of the chalcone synthase encoded by the following: (a) nucleotide sequence derived from wheat clone wfl1c.pk001.k16:fis (SEQ ID NO:2), (b) nucleotide sequence derived from wheat clone wlm96.pk061.i14:fis (SEQ ID NO:4); and (ii) amino acid sequence of *Juglans nigra×Juglans regia* chalcone synthase (NCBI General Identifier No. 1296816; SEQ ID NO:5). Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

| Chalcone Synthase | | | |
|---|---|---|---|
| | | SEQ ID NO: | |
| Protein | Clone Designation | Nucleotide | Amino Acid |
| Wheat polypeptide similar to *Juglans nigra* × *Juglans regia* naringenin-chalcone synthase | wfl1c.pk001.k16:fis | 1 | 2 |
| Wheat polypeptide similar to *Juglans nigra* × *Juglans regia* naringenin-chalcone synthase | wlm96.pk061.i14:fis | 3 | 4 |

SEQ ID NO:5 is the amino acid sequence of *Juglans nigra×Juglans regia* (NCBI General Identifier No. 1296816).

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF PREFERRED EMBODIMENTS

The disclosure of each patent, patent application and non-patent literature in the instant specification is incorporated herein by reference in its entirety.

In the context of this disclosure, a number of terms shall be utilized.

"Chalcone synthase" is also known as naringenin-chalcone synthase, flavanone synthase, 6'-deoxychalcone synthase, chalcone synthetase and CHS.

The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NO:1 or 3, or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques. A "recombinant DNA construct" comprises any of the isolated polynucleotides of the present invention operably linked to at least one regulatory sequence.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence of SEQ ID NO:1 or 3, and the complement of such nucleotide sequences may be used to affect the expression and/or function of a chalcone synthase in a host cell. A method of using an isolated polynucleotide to affect the level of expression of a polypeptide in a host cell (eukaryotic, such as plant or yeast, prokaryotic such as bacterial) may comprise the steps of: constructing an isolated polynucleotide of the present invention or an isolated recombinant DNA construct of the present invention; introducing the isolated polynucleotide or the isolated recombinant DNA construct into a host cell; measuring the level of a polypeptide or enzyme activity in the host cell containing the isolated polynucleotide; and comparing the level of a polypeptide or enzyme activity in the host cell containing the isolated polynucleotide with the level of a polypeptide or enzyme activity in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are preferably at least 70% identical, more preferably at least 80% identical to the amino acid sequences reported herein. More preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above identities but typically encode a polypeptide having preferably at least 50 amino acids, more preferably at least 100 amino acids, more preferably at least 150 amino acids, still more preferably at least 200 amino acids, and most preferably at least 250 amino acids.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention includes the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, recombinant DNA constructs, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) Ann. Rev. Plant Phys. Plant Mol. Biol. 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) Plant Phys. 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) Meth. Enzymol. 143:277; Ishida Y. et al. (1996) Nature Biotech. 14:745–750) and particle-accelerated or "gene gun" transformation technology (Klein et al. (1987) Nature (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

The terms "recombinant construct", "expression construct" and "recombinant expression construct" are used interchangeably herein. These terms refer to a functional unit of genetic material that can be inserted into the genome of a cell using standard methodology well known to one skilled in the art. Such construct may be used by itself or may be used in conjunction with a vector. If a vector is used, the choice of vector is dependent upon the method that will be used to transform host plants as is well known to those skilled in the art.

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

"Motifs" or "subsequences" refer to short regions of conserved sequences of nucleic acids or amino acids that comprise part of a longer sequence. For example, it is expected that such conserved subsequences would be important for function, and could be used to identify new homologues in plants. It is expected that some or all of the elements may be found in a homologue. Also, it is expected that one or two of the conserved amino acids in any given motif may differ in a true homologue.

"PCR" or "polymerase chain reaction" is well known by those skilled in the art as a technique used for the amplification of specific DNA segments (U.S. Pat. Nos. 4,683,195 and 4,800,159).

Polynucleotides of the present invention may be used in plant cells to control plant reproduction, in particular male fertility (see U.S. Pat. No. 6,037,523). Furthermore, overexpression of chalcone synthase may result in an increase of compounds in flavonoid classes. More specifically, chalcone synthase overexpression may result in an increase in levels of 4,2',4'-trihydroxyflavone and 4,2',4',6'-tetrahydroxyflavone, precursors in the biosynthetic pathways leading to isoflavone, flavone and dihydroflavanol (which upon continuation leads to anthocyanin and flavanols) synthesis (see FIG. 1). Increased isoflavone content in legumes has been shown to be associated with beneficial health effects in humans.

The present invention includes an isolated polynucleotide comprising a nucleotide sequence encoding a chalcone synthase polypeptide having at least 80% identity, based on the Clustal method of alignment, when compared to a polypeptide of SEQ ID NO:2 or 4.

This invention also includes the isolated complement of such polynucleotides, wherein preferably the complement and the polynucleotide consist of the same number of nucleotides, and the nucleotide sequences of the complement and the polynucleotide have 100% complementarity.

Nucleic acid fragments encoding at least a portion of several chalcone synthase proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other chalcone synthase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of preferably at least 30 (more preferably at least 40, most preferably at least 60) contiguous nucleotides derived from a nucleotide sequence of SEQ ID NOs:1 or 3, and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another preferrred embodiment, this invention includes viruses and host cells comprising either the recombinant DNA constructs of the invention as described herein or isolated polynucleotides of the invention as described herein. Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the proportion of sterol to sterol glucoside in those cells which is very important in determining membrane fluidity. Additionally, genes of the instant invention may be used to screen and identify natural or synthetic herbicidal or fungicidal compounds. Furthermore, the relatively few chalcone synthases identified in eukaryotic organisms has chalcone synthase as an attractive target for the design of novel antibacterial agents. Accordingly, the availability of nucleic acid sequences encoding all or a portion of the enzyme chalcone synthase would facilitate studies to better understand lipid metabolism in plants and provide genetic tools to alter its role.

The regeneration, development and cultivation of plants from single plant protoplast transformants or from various transformed explants is well known in the art (Weissbach and Weissbach, In, Methods for Plant Molecular Biology, (Eds.), Academic Press, Inc., San Diego, Calif. (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a protein of interest is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

There are a variety of methods for the regeneration of plants from plant tissue. The particular method of regeneration will depend on the starting plant tissue and the particular plant species to be regenerated. Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011, McCabe et. al., *BiolTechnology*6:923 (1988), Christou et al., *Plant Physiol.* 87:671–674 (1988)); *Brassica* (U.S. Pat. No. 5,463,174); peanut (Cheng et al., *Plant Cell Rep.* 15:653–657 (1996), McKently et al., *Plant Cell Rep.* 14:699–703 (1995)); papaya; and pea (Grant et al., Plant Cell Rep. 15:254–258, (1995)).

Transformation of monocotyledons using electroporation, particle bombardment, and Agrobacterium have also been reported. Transformation and plant regeneration have been achieved in asparagus (Bytebier et al., *Proc. Natl. Acad. Sci.* (USA) 84:5354, (1987)); barley (Wan and Lemaux, *Plant Physiol* 104:37 (1994)); *Zea mays* (Rhodes et al., *Science* 240:204 (1988), Gordon-Kamm et al., *Plant Cell* 2:603–618 (1990), Fromm et al., *BiolTechnology* 8:833 (1990), Koziel et al., *BiolTechnology* 11: 194, (1993), Armstrong et al., *Crop Science* 35:550–557 (1995)); oat (Somers et al., *BiolTechnology* 10: 15 89 (1992)); orchard grass (Horn et al., *Plant Cell Rep.* 7:469 (1988)); rice (Toriyama et al., *TheorAppl. Genet.* 205:34, (1986); Part et al., *Plant Mol. Biol.* 32:1135–1148, (1996); Abedinia et al., *Aust. J. Plant Physiol.* 24:133–141 (1997); Zhang and Wu, *Theor. Appl. Genet.* 76:835 (1988); Zhang et al. *Plant Cell Rep.* 7:379, (1988); Battraw and Hall, *Plant Sci.* 86:191–202 (1992); Christou et al., *Bio/Technology* 9:957 (1991)); rye (De la Pena et al., *Nature* 325:274 (1987)); sugarcane (Bower and Birch, *Plant J.* 2:409 (1992)); tall fescue (Wang et al., *BiolTechnology* 10:691 (1992)), and wheat (Vasil et al., *Bio/Technology* 10:667 (1992); U.S. Pat. No. 5,631,152).

Assays for gene expression based on the transient expression of cloned nucleic acid constructs have been developed by introducing the nucleic acid molecules into plant cells by polyethylene glycol treatment, electroporation, or particle bombardment (Marcotte et al., *Nature* 335:454–457 (1988); Marcotte et al., *Plant Cell* 1:523–532 (1989); McCarty et al., *Cell* 66:895–905 (1991); Hattori et al., *Genes Dev.* 6:609–618 (1992); Goff et al., *EMBO J.* 9:2517–2522 (1990)).

Transient expression systems may be used to functionally dissect gene constructs (see generally, Maliga et al., Methods in Plant Molecular Biology, Cold Spring Harbor Press (1995)). It is understood that any of the nucleic acid molecules of the present invention can be introduced into a plant cell in a permanent or transient manner in combination with other genetic elements such as vectors, promoters, enhancers etc.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Maliga et al., Methods in Plant Molecular Biology, Cold Spring Harbor Press (1995); Birren et al., Genome Analysis: Detecting Genes, 1, Cold Spring Harbor, N.Y. (1998); Birren et al., Genome Analysis: Analyzing DNA, 2, Cold Spring Harbor, N.Y. (1998); Plant Molecular Biology: A Laboratory Manual, eds. Clark, Springer, N.Y. (1997)).

Overexpression of the proteins of the instant invention may be accomplished by first constructing a recombinant DNA construct in which the coding region is operably linked to a promoter capable of directing expression of a gene in the desired tissues at the desired stage of development. The recombinant DNA construct may comprise promoter sequences and translation leader sequences derived from the same genes. 3' Non-coding sequences encoding transcription termination signals may also be provided. The instant recombinant DNA construct may also comprise one or more introns in order to facilitate gene expression.

Plasmid vectors comprising the instant isolated polynucleotide(s) (or recombinant DNA construct(s)) may be constructed. The choice of plasmid vector is dependent upon the method that will be used to transform host plants. The skilled artisan is well aware of the genetic elements that must be present on the plasmid vector in order to successfully transform, select and propagate host cells containing the recombinant DNA construct or chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the recombinant DNA construct(s) described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100: 1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a recombinant DNA construct designed for co-suppression of the instant polypeptide can be constructed by linking a gene or gene fragment encoding that polypeptide to plant promoter sequences. Alternatively, a recombinant DNA construct designed to express antisense RNA for all or part of the instant nucleic acid fragment can be constructed by linking the gene or gene fragment in reverse orientation to plant promoter sequences. Either the co-suppression or antisense recombinant DNA constructs could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different recombinant DNA constructs utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

In another preferred embodiment, the present invention includes a chalcone synthase polypeptide having an amino acid sequence that is at least 80% identical, based on the Clustal method of alignment, to a polypeptide of SEQ ID NO:2 or 4.

The instant polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA construct for production of the instant polypeptides. This recombinant DNA construct could then be introduced into appropriate microorganisms via transformation to provide high level expression of the encoded chalcone synthase. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) Plant Mol. Biol. Reporter 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several kb to several hundred kb; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.*

17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further illustrated in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

EXAMPLE 1

Composition of cDNA Libraries Isolation and Sequencing of cDNA Clones cDNA libraries representing mRNAs from wheat (*Triticum aestivum*) tissues were prepared. The characteristics of the libraries are described below.

TABLE 2 cDNA Libraries from Wheat

| Library | Tissue | Clone |
|---------|--------|-------|
| wfl1c | Wheat (*Triticum aestivum*, Hi Line) flag leaf | wfl1c.pk001.k16:fis |
| wlm96 | Wheat (*Triticum aestivum*) Seedlings 96 Hours After Inoculation With *Erysiphe graminis* f. sp tritici | wlm96.pk061.i14:fis | cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phred/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

EXAMPLE 2

Identification of cDNA Clones cDNA clones encoding chalcone synthase were identified by conducting BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health) searches for similarity to sequences contained in the BLAST "nr" database (comprising all non-redundant GenBank™ CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the GenBank™ database as described above. ESTs that contain sequences more 5- or 3-prime can be found by using the BLASTn algorithm (Altschul et al (1997) *Nucleic Acids Res.* 25:3389–3402.) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

EXAMPLE 3

Characterization of cDNA Clones Encoding Chalcone Synthase

The BLASTX search using the EST sequences from clones listed in Table 3 revealed similarity of the polypeptides encoded by the cDNAs to naringenin-chalcone synthase from *Juglans nigra×Juglans regia* (NCBI General Identifier No.1296816; SEQ ID NO:5). Shown in Table 3 are the BLAST results for individual ESTs ("EST"), the sequences of contigs assembled from two or more ESTs ("Contig"), the sequences of the entire cDNA inserts comprising the indicated cDNA clones ("FIS"), or sequences encoding an entire protein derived from an FIS, a contig, or an FIS and PCR ("CGS"):

TABLE 3

BLAST Results for Sequences Encoding Polypeptides Homologous to Chalcone Synthase

| Clone | Status | NCBI General Identifier No. (SEQ ID NO:) | BLAST pLog Score |
|---|---|---|---|
| wfl1c.pk001.k16:fis | CGS | 1296816 (SEQ ID NO: 5) | 113.00 |
| wlm96.pk061.i14:fis | CGS | 1296816 (SEQ ID NO: 5) | 117.00 |

The nucleotide sequence of the entire cDNA insert in clone wfl1c.pk001.k16:fis is shown in SEQ ID NO:1. The amino acid sequence deduced from nucleotides 104 through 1303 of SEQ ID NO:1 is shown in SEQ ID NO:2. The nucleotide sequence of the entire cDNA insert in clone wlm96.pk061.i14:fis is shown in SEQ ID NO:3. The amino acid sequence deduced from nucleotides 1 through 1167 of SEQ ID NO:3 is shown in SEQ ID NO:4.

FIGS. 2A and 2B present an alignment of the amino acid sequences set forth in SEQ ID NOs:2, 4 and the sequence from *Juglans nigra×Juglans regia* (NCBI General Identifier No. 1296816; SEQ ID NO:5). The data in Table 4 represents a calculation of the percent identity of the amino acid sequences set forth in SEQ ID NOs:2, 4 and the sequence from *Juglans nigra×Juglans regia* (NCBI General Identifier No. 1296816; SEQ ID NO:5).

TABLE 4

Percent Identity of Amino Acid Sequences Deduced From the Nucleotide Sequences of cDNA Clones Encoding Polypeptides Homologous to Chalcone Synthase

| Clone | SEQ ID NO: | NCBI General Identifier No. (SEQ ID NO:) | Percent Identity to |
|---|---|---|---|
| wfl1c.pk001.k16:fis | 2 | 1296816 (SEQ ID NO: 5) | 50.6 |
| wlm96.pk061.i14:fis | 4 | 1296816 (SEQ ID NO: 5) | 51.4 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a chalcone synthase.

Example 4

Expression of Recombinant DNA Constructs in Monocot Cells

A recombinant DNA construct comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110–2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a recombinant DNA construct encoding, in the 5' to 3' direction, the maize 27 kD zein promoter, a cDNA fragment encoding the instant polypeptides, and the 10 kD zein 3' region.

The recombinant DNA construct described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from cauliflower mosaic virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Recombinant DNA Constructs in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from cauliflower mosaic virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Recombinant DNA Constructs in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and Hind III sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Furthermore, assays for chalcone synthase are presented by Zuurbier et al., (*Phytochemistry* 34(5):1225–1229 (1993)) and Claudot et al., (*Phytochemistry* 31(10):3377–3380 (1992)).

What is claimed is:

1. An isolated polynucleotide comprising:
   (a) a nucleotide sequence encoding a polypeptide having chalcone synthase activity, wherein the amino acid sequence of the polypeptide and the amino acid sequence of SEQ ID NO:2 have at least 90% sequence identity, or
   (b) the full-length complement of the nucleotide sequence of (a).

2. The polynucleotide of claim 1, wherein the amino acid sequence of the polypeptide and the amino acid sequence of SEQ ID NO:2 have at least 95%.

3. The polynucleotide of claim 1, wherein the amino acid sequence of the polypeptide comprises the amino acid sequence of SEQ ID NO:2.

4. The polynucleotide of claim 1 wherein the nucleotide sequence comprises the nucleotide sequence of SEQ ID NO:1.

5. A vector comprising the polynucleotide of claim 1.

6. A recombinant DNA construct comprising the polynucleotide of claim 1 operably linked to at least one regulatory sequence.

7. A method for transforming a cell, comprising transforming a cell with the polynucleotide of claim 1.

8. A cell comprising the recombinant DNA construct of claim 6.

9. A method for producing a plant comprising transforming a plant cell with the polynucleotide of claim 1 and regenerating a plant from the transformed plant cell.

10. A plant comprising the recombinant DNA construct of claim 6.

11. A seed comprising the recombinant DNA construct of claim 6.

* * * * *

SEQUENCE LISTING

<160> NUMBER OF SEQ ID NOS: 5

<210> SEQ ID NO 1
<211> LENGTH: 1540
<212> TYPE: DNA
<213> ORGANISM: Triticum aestivum

<400> SEQUENCE: 1

```
aattacccgg gctgcaggaa ttcggcacga ggcaatcttg aagcagtttt ctccctctcg      60
tccatctcaa taagtgcccg cttcttaatt aggctccgag gccatgggca gcaacaccct     120
tacgtcgatg cacgagatcc ggcgcttgca gcgtgccgag gggcctgcgg ccatcctcgc     180
cgtcggcacc gcgaacccgc ccaactgcgt gtcccaggag gagtacccgg actactactt     240
ccgcgtcacc aagagcgagc acctcaccga cctcaaacaa aagctcaagt ccttctgcca     300
gatgacctca acggagaagc gctacttcca ccacacggag gagctgctgg acgcccaccc     360
agaattcctc cgccgcgaca cgccgtccct ggacgcccgg ctggacatcg ccgctgccgc     420
tgctccagag ctcgcggcgt cagccgcagc caaggccata gccgagtggg gccgtccggc     480
caccgacatc acccacctcg tcgtcagcac caactccggc gcgcacgccc cgggcgtcga     540
ccttcgcctg gcctctctcc tcggcctccg cgcatccgtt tgccggacga tgctcaacct     600
caacggctgc tcggccggtg cggcctcgct gcgcctggcc aaggacctgg ccgagaacaa     660
ccgcggcgca cgcgtcctgg tggcctgcgt cgagctcacc gtcgtcgcct tccgcgggcc     720
cgaggaggcg tacccacaca ggctcatcag ccaggcgatc tttggtgacg gcgcaggcgc     780
ggtcatcgtc ggcgctgacg ccgtgcgctc cgtcgagcgc ccgctcttcg agatggtgtc     840
ggcctcgcag accacgatac cagcaaccga cggcgtgctc accatgcagc tcacggaagc     900
cggcctcgac ggcgacatct tcaccaggga gctcacgcct ctagccgcgc agcacatcga     960
```

-continued

```
gcagtgtctc acggacgcgt tccagccgct tggaataatg agcggcggtg ccgaatggaa    1020
cgatctgttc tttgtggtgc accctggcct ccgtggaata atggaccaca tcgacggggc    1080
tctccggctg gatcccggga agctggtggc gagccggacc gtgctgagag agtacggcaa    1140
catgcttggc gcgacgctga tcttcgtgct cgacgagcaa cggcggcgga tggaggagga    1200
cggcgagacg ggtgagtggg gtgtgatgat gggatttgga ccagggttta cggttgagac    1260
catggtgctg catgcggtgg ccatcgacct gcacaacgag aattgaccct cgaccgattc    1320
ataaccttgc tactttctgt catatatata atttgaaaca aattaaaaat acgcaagtac    1380
aattgtaagc attcagatcg tacaacttgc tcgctagggc atcacagcat tcagatcatt    1440
ggagttgggt ggaataattt gtaggagtac aaggttatgg ttaatttgaa acttttgcca    1500
aaaaaaaaaa aaaaaaaaaa aaaaaaaaaa aaaaaaaaa                          1540
```

<210> SEQ ID NO 2
<211> LENGTH: 400
<212> TYPE: PRT
<213> ORGANISM: Triticum aestivum

<400> SEQUENCE: 2

```
Met Gly Ser Asn Thr Leu Thr Ser Met His Glu Ile Arg Arg Leu Gln
  1               5                  10                  15

Arg Ala Glu Gly Pro Ala Ala Ile Leu Ala Val Gly Thr Ala Asn Pro
             20                  25                  30

Pro Asn Cys Val Ser Gln Glu Glu Tyr Pro Asp Tyr Tyr Phe Arg Val
         35                  40                  45

Thr Lys Ser Glu His Leu Thr Asp Leu Lys Gln Lys Leu Lys Ser Phe
     50                  55                  60

Cys Gln Met Thr Ser Thr Glu Lys Arg Tyr Phe His His Thr Glu Glu
 65                  70                  75                  80

Leu Leu Asp Ala His Pro Glu Phe Leu Arg Arg Asp Thr Pro Ser Leu
                 85                  90                  95

Asp Ala Arg Leu Asp Ile Ala Ala Ala Ala Pro Glu Leu Ala Ala
            100                 105                 110

Ser Ala Ala Lys Ala Ile Ala Glu Trp Gly Arg Pro Ala Thr Asp
        115                 120                 125

Ile Thr His Leu Val Val Ser Thr Asn Ser Gly Ala His Ala Pro Gly
    130                 135                 140

Val Asp Leu Arg Leu Ala Ser Leu Leu Gly Leu Arg Ala Ser Val Cys
145                 150                 155                 160

Arg Thr Met Leu Asn Leu Asn Gly Cys Ser Ala Gly Ala Ala Ser Leu
                165                 170                 175

Arg Leu Ala Lys Asp Leu Ala Glu Asn Asn Arg Gly Ala Arg Val Leu
            180                 185                 190

Val Ala Cys Val Glu Leu Thr Val Val Ala Phe Arg Gly Pro Glu Glu
        195                 200                 205

Ala Tyr Pro His Arg Leu Ile Ser Gln Ala Ile Phe Gly Asp Gly Ala
    210                 215                 220

Gly Ala Val Ile Val Gly Ala Asp Ala Val Arg Ser Val Glu Arg Pro
225                 230                 235                 240

Leu Phe Glu Met Val Ser Ala Ser Gln Thr Thr Ile Pro Ala Thr Asp
                245                 250                 255

Gly Val Leu Thr Met Gln Leu Thr Glu Ala Gly Leu Asp Gly Asp Ile
            260                 265                 270
```

-continued

```
Phe Thr Arg Glu Leu Thr Pro Leu Ala Ala Gln His Ile Glu Gln Cys
        275                 280                 285
Leu Thr Asp Ala Phe Gln Pro Leu Gly Ile Met Ser Gly Gly Ala Glu
    290                 295                 300
Trp Asn Asp Leu Phe Phe Val Val His Pro Gly Leu Arg Gly Ile Met
305                 310                 315                 320
Asp His Ile Asp Gly Ala Leu Arg Leu Asp Pro Gly Lys Leu Val Ala
                325                 330                 335
Ser Arg Thr Val Leu Arg Glu Tyr Gly Asn Met Leu Gly Ala Thr Leu
            340                 345                 350
Ile Phe Val Leu Asp Glu Gln Arg Arg Met Glu Glu Asp Gly Glu
        355                 360                 365
Thr Gly Glu Trp Gly Val Met Met Gly Phe Gly Pro Gly Phe Thr Val
    370                 375                 380
Glu Thr Met Val Leu His Ala Val Ala Ile Asp Leu His Asn Glu Asn
385                 390                 395                 400
```

<210> SEQ ID NO 3
<211> LENGTH: 1317
<212> TYPE: DNA
<213> ORGANISM: Triticum aestivum

<400> SEQUENCE: 3

```
gcacgagggc gcgcgcagcg cgccgacggg ccggcggccg tgctcgccat cggcacggcg    60
aacccggcgc actgcgtgcc ccaggacgag ttcccggact tctacttccg cgccaccaac   120
agcgaccacc tcactgccct caagggcaag ttcaagagag tctttcagaa gctaggcgtt   180
gagaagcgct acctccacca cacggaggag ctgctgcgcg cccacccega gttcctcgac   240
gacgaggcgg cgtccctgga cgcccggctg gacatcgtcg ccaccgccgt cccggagctg   300
gccgcggagg cctctaagaa ggccatctcc gagtggggcc ggccggccgc cgacatcacc   360
cacctcgtgg tcaccacaaa ctccggcgcc cacatcccgg gcgtcgactt ccgcctcatc   420
ccgcttctcg gcctccgccc ctccgtgcgt cgcaccatgc tctacctcaa cggctgcttc   480
gccggctccg ccgcgctgcg cctcgccaag gacctcgccg agaacaaccg cggcgcgcgc   540
gtcctcgtgg tctgcgccga gctcacccte atgctgttca acgggcccaa ggagggctcc   600
ttcgagaggc tcatccacca ggggctcttc ggcgacggcg cgggcgccgt cgtcgtcggc   660
gccgacccgc tgagccccgt cgagcacgcc ctgttcgaga tggtgtccgc cgcgcagacg   720
gtgataccgg actccggcga cgccatcacc atgcacatca ccaagggcgg gttcggcggc   780
aacatctcca cgagggacgt cccggtgttc attggggaca acgtcgagcg gtgcctccac   840
gactcgctgg agccgctcgg catcggcgcg aaatggaacg acctcttctg gcggtgcac    900
cccgggtcgt ctgccattct ggaccgcatc gacacggtgc tccagctcga gccggagaag   960
ctggcggcga gccgccgggt gctgagcgac tacgcaaca tgttcggcgt gacaattata  1020
tttgttctcg acgagctgcg ccggaggctt agggagcagg aagggccgg cggcgcgccg  1080
gagtggggtg tggtgatgac cttcgggccg gggctcaccg tggagacgat ggtgttgcac  1140
gccactgggc acatgcatgc gtccccatga agaggaattg acactggatt aagaggtcaa  1200
ttcgttgtat cagtttgcac ttatttggca ctgtttgaag tcgtttacca aaaccatcct  1260
tacttgaatg tgtgcgtaat aaagtcaaag ttcaataaaa aaaaaaaaaa aaaaaaa     1317
```

<210> SEQ ID NO 4
<211> LENGTH: 389

```
<212> TYPE: PRT
<213> ORGANISM: Triticum aestivum

<400> SEQUENCE: 4

Ala Arg Gly Arg Ala Gln Arg Ala Asp Gly Pro Ala Ala Val Leu Ala
 1               5                  10                  15

Ile Gly Thr Ala Asn Pro Ala His Cys Val Pro Gln Asp Glu Phe Pro
            20                  25                  30

Asp Phe Tyr Phe Arg Ala Thr Asn Ser Asp His Leu Thr Ala Leu Lys
        35                  40                  45

Gly Lys Phe Lys Arg Val Phe Gln Lys Leu Gly Val Glu Lys Arg Tyr
    50                  55                  60

Leu His His Thr Glu Glu Leu Leu Arg Ala His Pro Glu Phe Leu Asp
65                  70                  75                  80

Asp Glu Ala Ala Ser Leu Asp Ala Arg Leu Asp Ile Val Ala Thr Ala
                85                  90                  95

Val Pro Glu Leu Ala Ala Glu Ala Ser Lys Lys Ala Ile Ser Glu Trp
            100                 105                 110

Gly Arg Pro Ala Ala Asp Ile Thr His Leu Val Val Thr Thr Asn Ser
        115                 120                 125

Gly Ala His Ile Pro Gly Val Asp Phe Arg Leu Ile Pro Leu Leu Gly
    130                 135                 140

Leu Arg Pro Ser Val Arg Arg Thr Met Leu Tyr Leu Asn Gly Cys Phe
145                 150                 155                 160

Ala Gly Ser Ala Ala Leu Arg Leu Ala Lys Asp Leu Ala Glu Asn Asn
                165                 170                 175

Arg Gly Ala Arg Val Leu Val Val Cys Ala Glu Leu Thr Leu Met Leu
            180                 185                 190

Phe Asn Gly Pro Lys Glu Gly Ser Phe Glu Arg Leu Ile His Gln Gly
        195                 200                 205

Leu Phe Gly Asp Gly Ala Gly Ala Val Val Val Gly Ala Asp Pro Leu
    210                 215                 220

Ser Pro Val Glu His Ala Leu Phe Glu Met Val Ser Ala Ala Gln Thr
225                 230                 235                 240

Val Ile Pro Asp Ser Gly Asp Ala Ile Thr Met His Ile Thr Lys Gly
                245                 250                 255

Gly Phe Gly Gly Asn Ile Ser Thr Arg Asp Val Pro Val Phe Ile Gly
            260                 265                 270

Asp Asn Val Glu Arg Cys Leu His Asp Ser Leu Glu Pro Leu Gly Ile
        275                 280                 285

Gly Ala Lys Trp Asn Asp Leu Phe Trp Ala Val His Pro Gly Ser Ser
    290                 295                 300

Ala Ile Leu Asp Arg Ile Asp Thr Val Leu Gln Leu Glu Pro Glu Lys
305                 310                 315                 320

Leu Ala Ala Ser Arg Arg Val Leu Ser Asp Tyr Gly Asn Met Phe Gly
                325                 330                 335

Val Thr Ile Ile Phe Val Leu Asp Glu Leu Arg Arg Arg Leu Arg Glu
            340                 345                 350

Gln Glu Gly Ala Gly Gly Ala Pro Glu Trp Gly Val Val Met Thr Phe
        355                 360                 365

Gly Pro Gly Leu Thr Val Glu Thr Met Val Leu His Ala Thr Gly His
    370                 375                 380

Met His Ala Ser Pro
385
```

<210> SEQ ID NO 5
<211> LENGTH: 389
<212> TYPE: PRT
<213> ORGANISM: Juglans nigra x Juglans regia

<400> SEQUENCE: 5

Met Val Thr Val Glu Asp Val Arg Arg Ala Gln Arg Ala Glu Gly Pro
 1               5                  10                  15

Ala Thr Val Met Ala Ile Gly Thr Ala Thr Pro Pro Asn Cys Val Asp
                20                  25                  30

Gln Ser Ala Tyr Pro Asp Tyr Tyr Phe Arg Ile Thr Asn Ser Glu His
            35                  40                  45

Lys Thr Glu Leu Lys Glu Lys Phe Lys Arg Met Cys Glu Lys Ser Met
        50                  55                  60

Ile Lys Lys Arg Tyr Met His Leu Thr Glu Glu Ile Leu Lys Glu Asn
65                  70                  75                  80

Pro Asn Val Cys Ala Tyr Met Ala Ser Ser Leu Asp Ala Arg Gln Asp
                85                  90                  95

Met Val Val Glu Val Pro Lys Leu Gly Lys Glu Ala Ala Thr Lys
               100                 105                 110

Ala Ile Lys Glu Trp Gly Gln Pro Lys Ser Lys Ile Thr His Leu Val
            115                 120                 125

Phe Cys Thr Thr Ser Gly Val Asp Met Pro Gly Ala Asp Tyr Gln Leu
        130                 135                 140

Thr Lys Leu Leu Gly Leu Arg Pro Ser Val Lys Arg Leu Met Met Tyr
145                 150                 155                 160

Gln Gln Gly Cys Phe Ala Gly Gly Thr Val Leu Arg Leu Ala Lys Asp
                165                 170                 175

Leu Ala Glu Asn Asn Lys Gly Ala Arg Val Leu Val Val Cys Ser Glu
            180                 185                 190

Ile Thr Ala Val Thr Phe Arg Gly Pro Ser Asp Thr His Leu Asp Ser
        195                 200                 205

Leu Val Gly Gln Ala Leu Phe Gly Asp Gly Ala Ala Ala Leu Ile Val
    210                 215                 220

Gly Ala Asp Pro Val Pro Gly Val Glu Lys Pro Leu Phe Glu Leu Val
225                 230                 235                 240

Ser Ala Ala Gln Thr Ile Leu Pro Asp Ser Asp Gly Ala Ile Asp Gly
                245                 250                 255

His Leu Arg Glu Val Gly Leu Thr Phe His Leu Leu Lys Asp Val Pro
            260                 265                 270

Gly Leu Ile Ser Lys Asn Ile Glu Lys Ser Leu Val Glu Ala Phe Gln
        275                 280                 285

Pro Leu Gly Ile Thr Asp Trp Asn Ser Leu Phe Trp Ile Ala His Pro
    290                 295                 300

Gly Gly Pro Ala Ile Leu Asp Gln Val Glu Ser Lys Leu Glu Leu Lys
305                 310                 315                 320

Pro Glu Lys Leu Arg Ala Thr Arg His Val Leu Ser Glu Tyr Gly Asn
                325                 330                 335

Met Ser Ser Ala Cys Val Leu Phe Ile Leu Asp Glu Met Arg Lys Lys
            340                 345                 350

Ser Ala Glu Asp Arg Leu Lys Thr Thr Gly Glu Gly Leu Glu Trp Gly
        355                 360                 365

Val Leu Phe Gly Phe Gly Pro Gly Leu Thr Val Glu Thr Val Val Leu

-continued

```
                370                 375                 380
His Ser Val Ser Ala
385
```